Figure 2:
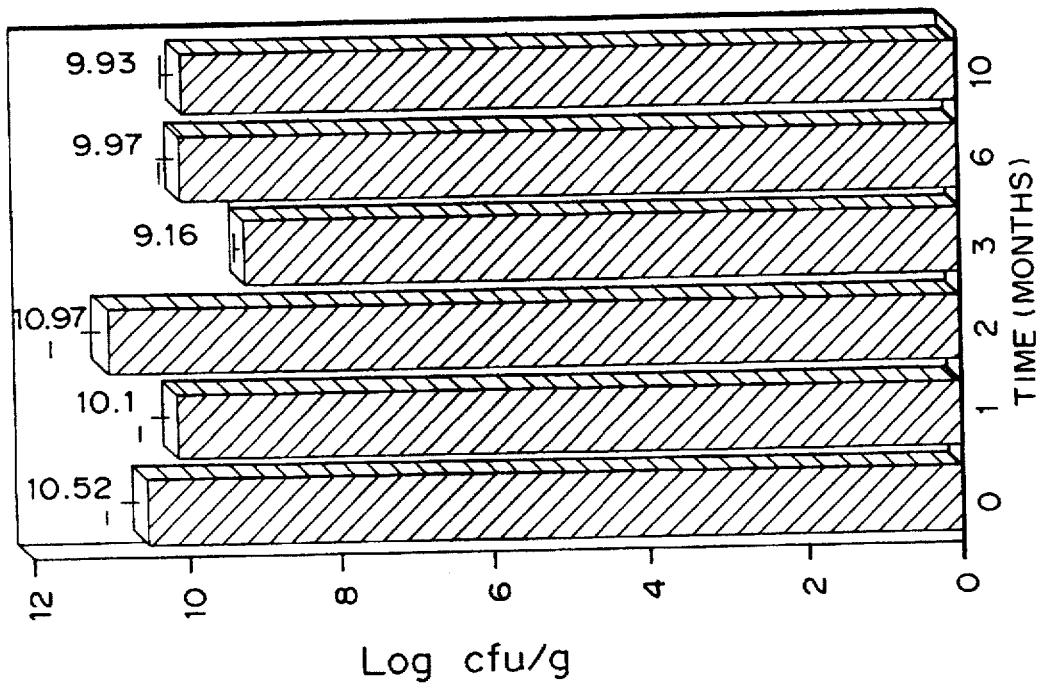
Figure 1:
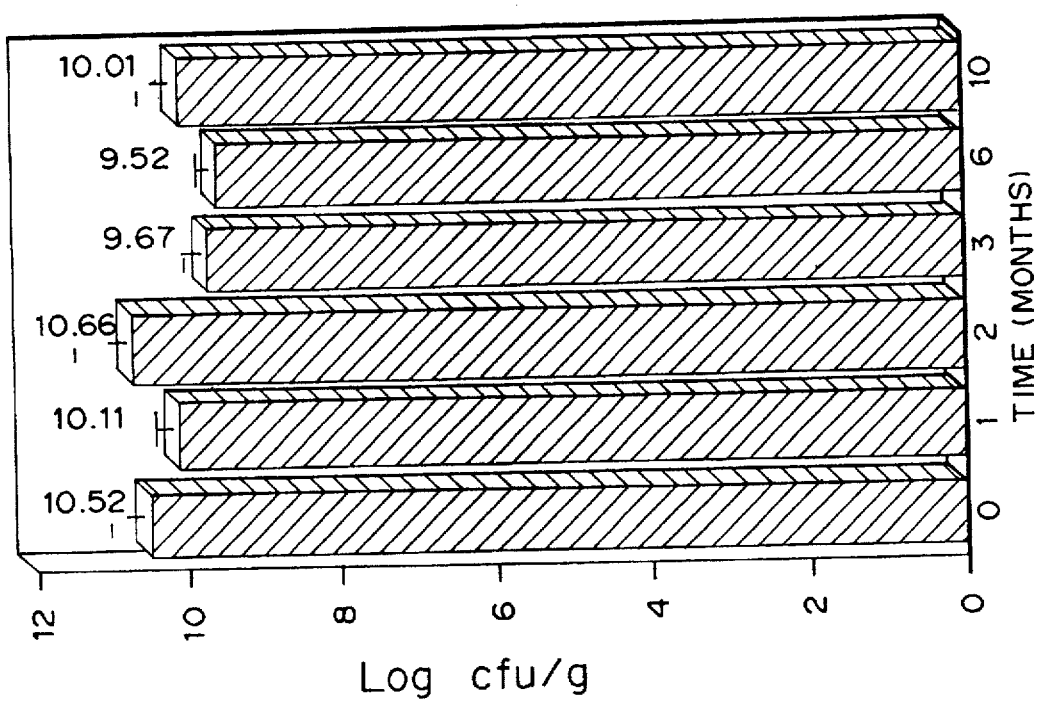

United States Patent [19]
Jin et al.

[11] Patent Number: 5,733,774
[45] Date of Patent: Mar. 31, 1998

[54] METHOD AND COMPOSITION FOR PRODUCING STABLE BACTERIA AND BACTERIAL FORMULATIONS

[75] Inventors: Xixuan Jin; Kathryn Grigas, both of Worcester; Chao Chen, Shrewsbury; Aparajit Panda, Westboro; Michael L. Matheny, Groton, all of Mass.

[73] Assignee: EcoScience Corporation, East Brunswick, N.J.

[21] Appl. No.: 382,688

[22] Filed: Feb. 2, 1995

[51] Int. Cl.$^6$ .................................................. C12N 5/00
[52] U.S. Cl. .......................... 435/260; 435/243; 435/245
[58] Field of Search ..................................... 435/260, 243, 435/245

[56] References Cited

U.S. PATENT DOCUMENTS

| | | | |
|---|---|---|---|
| 3,897,307 | 7/1975 | Porubcan et al. | 426/61 |
| 4,927,763 | 5/1990 | Sudoma et al. | 435/260 |
| 4,937,763 | 6/1990 | Sudoma et al. | 435/252.1 |
| 4,956,295 | 9/1990 | Sudoma | 435/252.1 |
| 5,089,407 | 2/1992 | Baker et al. | 435/179 |
| 5,296,221 | 3/1994 | Mitsuoka et al. | 435/243 |

FOREIGN PATENT DOCUMENTS

| | | |
|---|---|---|
| 0 203 708 A1 | 12/1986 | European Pat. Off. |
| 0 314 439 A2 | 5/1989 | European Pat. Off. |
| 2 394 606 A2 | 1/1979 | France |
| 2 592 892 A2 | 8/1987 | France |

OTHER PUBLICATIONS

Chen M. and M. Alexander, "Survival of Soil Bacteria During Prolonged Desiccation," *Soil Biol Biochem* 5:231–221 (1973).

Mary, Patrice, et al., "Rates of Drying and Survival of *Rhizobium meliloti* Strains during Storage at Different Relative Humidities," *App. and Environ. Microbiol.* 50:207–211 (1985).

Potts, Malcolm, "Desiccation Tolerance of Prokaryotes," *Microbiological Reviews* 755–805 (1994).

Webb, S.J., "Effect of Dehydration on Bacterial Recombination," *Nature* 217:1231–1234 (1968).

Webb. S.J., "The Effects of Oxygen on the Possible Repair of Dehydration Damage by *Escherchia coli*" *J. Gen. Microbiol.* 58:317–326 (1969).

*Primary Examiner*—Leon B. Lankford, Jr.
*Attorney, Agent, or Firm*—Arnall Golden & Gregory, LLP

[57] ABSTRACT

Stabilized bacteria and bacterial formulations which can survive long term storage at high temperature are described. Bacteria are dried until they reach a dormant state. Oxygen is then removed from the environment surrounding the bacteria to prevent oxidative damage to the dormant cells. The bacteria is packaged and stored in material impermeable to gas and water vapor until such time as it is ready for use. Bacteria stored under these conditions will remain stable and efficacious for at least a year.

19 Claims, 4 Drawing Sheets

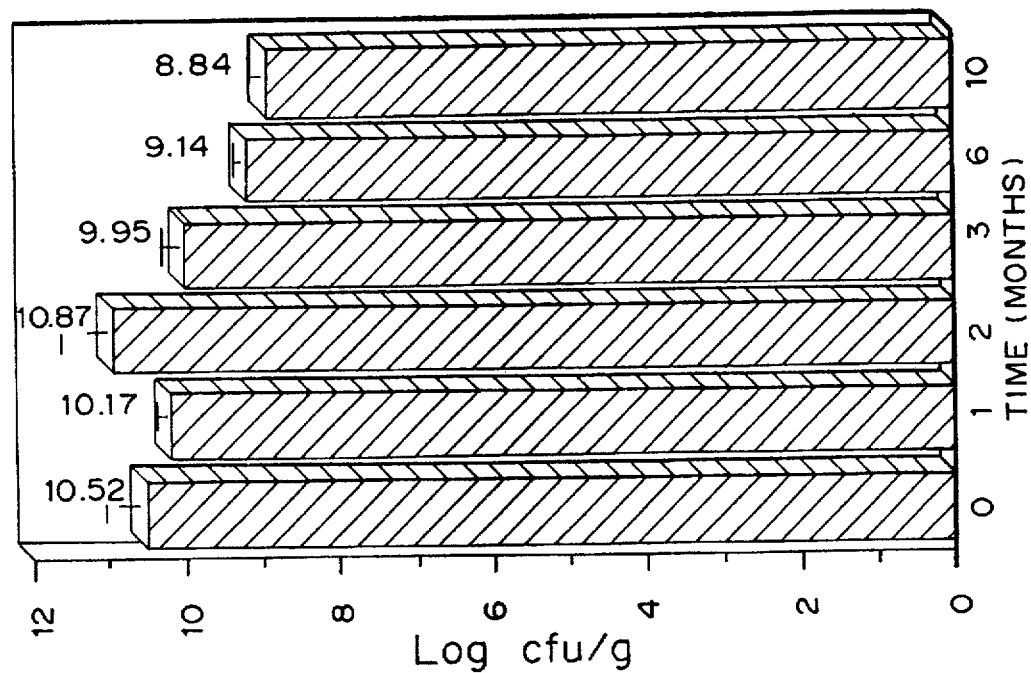
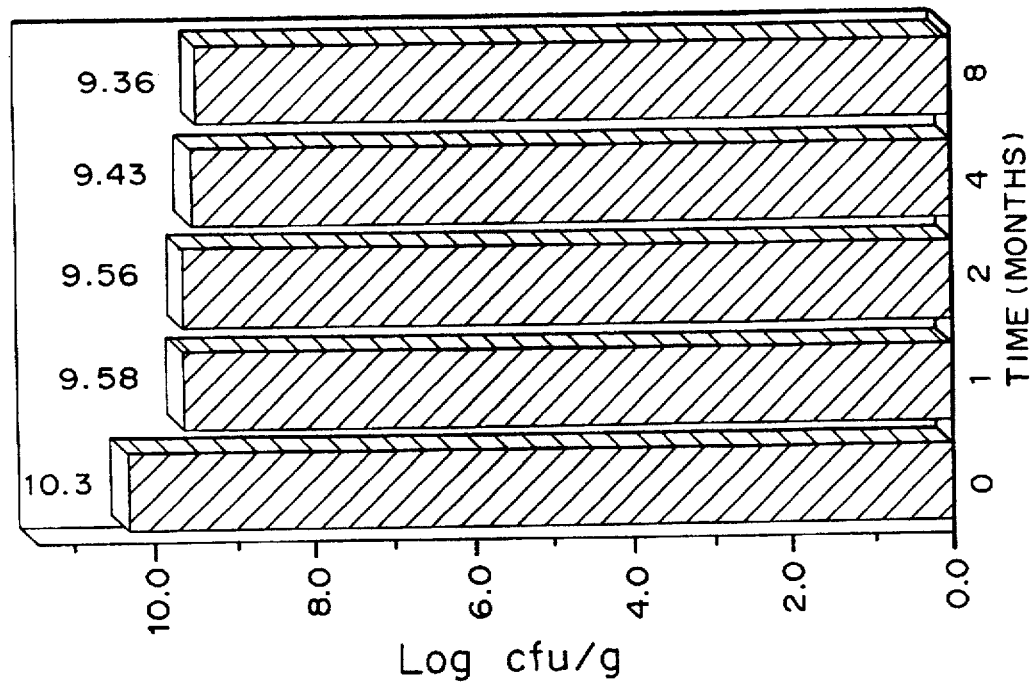

METHOD AND COMPOSITION FOR PRODUCING STABLE BACTERIA AND BACTERIAL FORMULATIONS

BACKGROUND OF THE INVENTION

This invention is generally in the area of long term stabilization of microorganisms.

Bacterial agents, including bacteria and bacterial formulations, are used in many applications including bioremediation, composting, cheese curing, microbial mining, sewage and waste water treatment and as biocontrol agents for the control of plant and insect pathogens. Bacterial agents are a promising alternative to highly toxic chemicals. However, developing standard formulations of bacterially based products such as the biological control agents available as replacements for chemical pesticides and fungicides has been particularly difficult. Although it is currently possible to maintain bacteria and bacterial agents in long term storage, such as in a culture collection, these organisms must be maintained at low temperatures and typically in liquid nitrogen. The organisms have a very limited shelf life once they are returned to room temperature or higher temperatures.

Significant losses of viable bacteria is not a problem in many cases, for example, when the bacteria is regrown prior to its intended use. However, loss of viable bacteria is a major problem in commercial applications when the bacterial agents must be stored at room or higher temperatures and then used without the need to grow additional material from the stored product. No system is currently available for storage of bacteria under ordinary room conditions.

This inability to maintain bacteria and bacterial agents for long periods of time at high temperatures currently limits the usefulness of bacterial agents. Many of the reported bacterial formulations must be stored at temperatures below 4° C., which is clearly impractical for most agricultural or other commercial applications. In addition, many of the currently available formulation contain significant amounts of water, which adds both volume and weight to products and makes them expensive to distribute. Moisture also decreases the long-term stability of the bacteria when stored at higher temperatures.

It is clearly impractical to store bacterial products under refrigerated conditions, especially when the agents must be loaded onto delivery trucks and stored in warehouses. Temperatures can be as high as 37° C. or even higher during transportation and warehouse storage. This has limited the commercial introduction of bacterial agents in many areas. In particular, it has prevented any large scale commercial introduction of bacterial biocontrol agents.

It is therefore an object of the present invention to provide a method and system to maintain the viability and increase the shelf-life of microorganisms, especially bacteria, when stored under the range of conditions found in commercial uses, especially elevated temperatures.

SUMMARY OF THE INVENTION

Specific conditions and formulation steps which lead to maximal stability of microorganisms such as bacteria have been developed which provide for long term, stable storage of the organisms under a variety of environmental conditions. It has been determined that bacteria in a dormant state and in a reduced oxygen environment can be maintained and kept viable for more than a year at room temperature.

Prior to packaging, the organisms are dried at temperatures which will not kill the microorganisms until free and bound water is removed. Suitable methods include air drying, vacuum drying, spray drying, flash drying, fluid bed drying, and controlled atmosphere drying. Packages are made of materials which are impermeable to oxygen and water vapor, such as aluminum foil and metalized polyesters. Low oxygen levels inside the package can be established using various methods, for example, vacuum sealing, vacuum with a subsequent flush of a gas such as nitrogen, or most preferably enclosing oxygen scavengers inside the package. Moisture can also be removed and/or low levels maintained by placing a desiccant in the packaging.

The microorganisms can be dried and formulated in combination with a carrier. Carriers can be combined with a surface active agent and/or dispersant to facilitate resuspension and application as a sprayable formulation. This combination can be stored and applied as either a dust, granule, wettable granule, wettable powder or as a tablet.

As demonstrated by the examples, the packaged bacterial formulations survive for a long period of time at 20° C., and at least more than ten months at elevated temperatures. These formulations are particularly useful for bacterial biocontrol agents for use in inhibiting plant pathogens.

BRIEF DESCRIPTION OF THE DRAWINGS

FIG. 1 is a graph of the stability of a 10% wettable powder formulation of *Pseudomonas syringae* in a foil pouch with Drierite® desiccant and Ageless® oxygen remover stored at 5° C. for 10 months, at intervals of 1, 2, 3, 6 and 10 months.

FIG. 2 is a graph of the stability of a 10% wettable powder formulation of *Pseudomonas syringae* in a foil pouch with Drierite® desiccant and Ageless® oxygen remover stored at 20° C. for ten months, at intervals of 1, 2, 3, 6 and 10 months.

FIG. 3 is a graph of the stability of a 10% wettable powder formulation of *Pseudomonas syringae* in a foil pouch with Drierite® desiccant and Ageless® oxygen remover stored at 25° C. for eight months, at intervals of 1, 2, 4 and 8 months.

FIG. 4 is a graph of the stability of a 10% wettable powder formulation of *Pseudomonas syringae* in a foil pouch with Drierite® desiccant and Ageless® oxygen remover stored at 30° C. for eight months, at intervals of 1, 2, 4 and 8 months.

FIG. 5 is a graph of the stability of a 10% wettable powder formulation of *Pseudomonas syringae* in foil pouch with Drierite® desiccant and Ageless® oxygen remover stored at 37° C. for eight months, at intervals of 1, 2, 4 and 8 months.

FIG. 6 is a graph of the stability of a 10% wettable powder formulation of *Pseudomonas syringae* in foil pouch with Drierite® desiccant and Ageless® oxygen remover stored at 25° C. and 37° C. and the same formulation in a foil pouch which had been vacuum packaged and stored at 25° C. and 37° C., at zero time and after four months.

FIG. 7 is a graph of the stability of an unpackaged 10% wettable powder formulation of *Pseudomonas syringae* stored at 25° C., at zero time, three weeks and six weeks.

DETAILED DESCRIPTION OF THE INVENTION

A method for producing stabilized bacterial compositions has been developed, which places the bacteria in a state of dormancy and serves to protect the bacteria from environmental elements which would negatively impact the viability of the bacteria. Cellular processes come to a halt during dormancy. Dormancy prevents the consumption and depletion of cellular food reserves at a time when no further nutrients are available. It will also largely, but not completely, prevent the aging of the organism that can lead to possible death.

The most standard way to bring on dormancy, either naturally or artificially, is through the removal of water. Organisms differ in their initial water content and the amount of water that must be removed to induce dormancy. However, general guidelines can be developed for this process. The essential goal is to remove sufficient water such that the natural cellular processes, for example, enzymatic activity, come to a halt. Water will be naturally removed from cells during air drying when the cells sit on a surface. At the level of process throughput and reproducibility required for commercial scale production, machines are used that remove water by various means, including vacuum drying, oven drying, spray drying, flash drying, fluid bed drying, and controlled atmosphere drying. The ideal process will occur at a high efficiency wherein water content is lowered to the appropriate level thorough water removal using processes that cause little loss in cell viability. Typically the correct level of water removal can be judged by assessing the water content of the cell during the time of the drying process. Water content will decrease to the point where free and bound water are largely removed and are reflected in a plateau when water content is plotted on a graph. Obtaining the plateau is a good point to proceed to and for bacteria this will typically occur at a water content of 10% or less. Drying can occur in the presence or absence of carriers. To maintain the achieved water content over the length of time desired for product shelf life requires placing the dried and formulated bacterial product into a largely impermeable package. Ideally the product will be placed in the bag along with a water removal device such as a Drierite package to further remove any excess water.

An additional essential feature for the long term stabilization of the bacteria is the removal of the oxygen. Active cells have many defensive mechanisms against the harmful effects of oxygen and its active derivatives such as peroxide and oxygen ions. Oxygen obviously cannot be removed from living aerobic cells. However, once dried and taken to a state of dormancy where they have no metabolic need for oxygen, these cells have little defense against these harmful effects. Over time these effects will have a significant negative impact. The highly efficient removal of oxygen will greatly improve the shelf stability of stored dried bacteria and their formulations. Essentially the more complete the removal of oxygen from dried bacterial the greater their shelf stability. Vacuum packaging achieves this to a degree, particular effective is the use of oxygen scavengers such as Ageless when introduced with the product into an essentially impermeable package for storage. In summary, the key elements of this invention are bringing bacterial cells to a level of dryness where they are brought to a state of dormancy identified by the leveling of the water content generally in a range below 10%. The cells brought to this state are then kept in this state of dormancy by packaging in an essentially impermeable package to prevent water vapor contact. The bacterial cells are further stabilized during their dormancy by protecting them from oxygen damage by removal of oxygen from the package. The higher the degree of oxygen removal the more stable the contents of the package.

The organisms packaged according to this invention are stable during long term storage at room temperatures or higher.

This process is in contrast to current methods for storage of bacteria. For example, the American Type Culture Collection, Rockville, Md., first lyophilizes and then stores bacteria under low oxygen conditions. However, both the cells and the water within the cells are frozen in this process which has low efficiency but in any event is most applicable to small volumes where speed is not a requirement. Bacteria processed under these conditions are usually refrigerated under low oxygen conditions for long term storage.

I. Microorganisms

Bacteria

Bacterial strains can be obtained from the American Type Culture Collection, Rockville, Md. Preferred bacteria for use as biocontrol agents include Pseudomonas species such as $P.$ $cepacia$ and $P.$ $syringae$, Enterobacter species, and Bacillus species such as $B.$ $thuringiensis$. A particularly preferred strain of $P.$ $syringae$ is ATCC 55389 for inhibiting microbial decay on fruits. Bacteria are cultured in a suitable liquid medium on a shaker flask. Alternatively, the bacteria can be cultured in a fermentation vessel containing a nutritionally-rich medium that is sufficient to support the growth of the organism.

The cultured bacteria are harvested, for example, by centrifugation or filtration, and then stored at about 4° C. or processed as described herein.

II. Formulations

Bacteria are typically produced by submerged fermentation. The resulting bacterial mass, or biomass, becomes the raw material for subsequent finishing steps leading to a biological control product. Bacteria may also be grown in a more immobilized, or solid state; in this situation, the bacteria are a more integral part of what could eventually be the carrier of the formulation.

Bacterial agents are typically formulated when they are to be used as commercial products. The formulation process puts the bacterial agent in a form where it is easy and convenient to use for its intended purpose. It is also ideal if the formulation process and method contributes to the stability of the product. Formulation can take many forms, including dusts, wettable powders, dry flowables, pellets, baits, and tablets. These formulations can be used for a variety of purposes, which in the case of bacterial biological control agents include plant disease, fruit disease and insect pest control.

In most cases, bacterial biomass is mixed with carriers prior to formulation and as part of the formulation process. The relative amounts of carrier to biomass will vary considerably depending upon the state of the biomass and/or the process being used. Spray drying will generally employ small amounts of carriers. Fluid bed drying can require significant amounts of carrier.

Carriers

Carriers can be either dry or liquid. Powder or granular inert materials may include plant growth media or matrices such as rockwool and peat-based mixes used for transplanting. Carriers may also include attapulgite clays, kaolinitc clays, montmorillonites, saponites, mica, perlites, vermiculite, and talcs, carbonates, sulfates, oxides such as silicon oxides diatomites, botanicals such as ground grains, soy flour, grain grits, wood pulp, and lignin, synthetic silicates such as precipitated hydrated calcium silicates and precipitated hydrated silicon dioxides, organics, polysaccharides such as cellulose-based gums, starches, seaweed extracts, alginates, plant gums, seed gums, plant extracts, microbial gums and any derivatives of polysaccharides, proteins, and synthetic polymers such as polyvinyl alcohols, polyvinyl pyrrolidone, polyacrylates and derivatives.

Surfactants and Dispersants

Surfactants and dispersants can be mixed with other carriers, such as clay, and bacteria prior to, or at the time of, or after drying to form a complete formulation for further application after storage.

Anionic, cationic, non-ionic, ampholytic and/or water-insoluble agents can be used as surfactants or dispersants. Nonionic surfactant include ethoxylated alcohols, ethoxylated alkyl phenols, ethoxylated alcohols, ethoxylated alkyl phenols, ethoxylated amines and amides, ethoxylated fatty acids, ethoxylated fatty esters and oils, glycerol esters, glycol esters, polymers of polysaccharides, polymers of acrylamides, propoxylated and ethoxylated fatty acids, alcohol phenols, alkyl phenols, sorbitan derivatives, sucrose and glucose esters, and block polymers including these moieties as components. Anionic surfactants include salts of sulfosuccinic acid, phosphate esters, and taurates.

Possible dispersants include salts of polyacrylic acids, sulfonic acids, sulfosuccinic acids, naphthalene sulfonic acids, benzene sulfonic acids, polymerized alkyl naphthalene sulfonic acids, and polymerized alkyl benzoate, alkyl sulfonic acids, phosphate esters, fatty acid esters, lignosulfonates and salts of lignin, polyethylene glycols, polycarboxylates, polysaccharides, polyvinyl pyrrolidones, chlorides, and carbonates.

III. Drying

There are three types of water in microorganisms: free water, bound water and preserved water. Free water is intercellular water and a part of the intracellular water. When free water is evaporated, the drying rate slows. Bound water is the part of intracellular water which combines directly with proteins, nucleic acids, membranes or other substances. Bound water is a component of the structural organization of these substances. The drying rate will decrease as bound water is removed, and reach a plateau when most all bound water has been removed. Preserved water is isolated in pockets formed by lipids and other membrane components and is resistant to drying. Stability of the microorganisms is increased when all free water has been removed. This is generally at the 20%–25% water content range.

Free water can be removed by various means, including air drying in a dry environment. However, the bound water must also be removed to achieve even greater stability. This can also take place via air drying. However in a commercial setting, usually steps are taken such as the addition of energy, to remove bound water from bacteria in a timely fashion. The preferred means of removing bound water is using a fluid bed dryer. When energy is added without a decrease in water content, it is an indication that most bound water has been removed and only the preserved water remains. This is generally in the 2 to 4% water content range. A significant increase in stability is observed when only one-half of the bound water remains, generally at the 10% water content range.

The microorganisms can be dried using any one of a variety of methods, including air drying, vacuum drying, oven drying, spray drying, flash drying, fluid bed drying, and controlled atmosphere drying. The preferred temperature for the drying process using a fluid bed dryer is between 40° C. and 140° C. The relative humidity of the air flow is between 0% and 30%.

IV. Packaging

Packaging Materials

A variety of materials having defined characteristics with regard to their barrier properties, that is, their ability to contain or allow the movement of differing gases through a layer of the material, are commercially available. These materials come in both rigid and flexible formats. Pouches made of flexible barrier films are readily available in a variety of properties and configurations. Materials which are substantially gas and water vapor impermeable materials are required to maintain the low humidity and oxygen requirements for the stabilized microorganism formulations described herein.

A preferred material for packaging bacteria is polyester-aluminum foil-polyethylene product #LF15015, a superior vapor barrier material which is commercially available from Laminated Foil and Packaging, Portsmouth, N.H. A polyester-aluminum foil-polyethylene bag having a thickness of 0.013 cm (0.005 in.), with an oxygen permeability of 0.0010 $cm^3$/645 $cm^2$/24 hr and a vapor permeability of 0.0010 g/645 $cm^2$/24 hr.

Similar materials that are commercially available can be substituted for the laminated foil to provide equivalent gas and water vapor impermeability.

Removal of Oxygen

Unformulated or formulated microorganisms are dried and stored in suitable packages (a) providing barriers to both oxygen and water vapor, and (b) maintaining low oxygen levels and low water content levels inside the packages. In the preferred embodiment, essentially all oxygen is removed from the package.

There are a variety of oxygen depleting agents, such as oxygen absorbers, that can be packaged with the bacteria to create a low oxygen environment. The oxygen absorbers used in removing oxygen in pouches or any other types of container, must be nontoxic to the bacteria. For example, Ageless™ is commercially available from the Mitsubishi International Corporation, Food division "B", 520 Madison Avenue, New York, N.Y. 10022. The major ingredient of Ageless™ is powdered active iron oxide which become iron oxides and hydroxides after absorption of oxygen. In an air-tight container, Ageless reduces oxygen down to 0.01% (100 ppm) or less. Oxygen absorbers selected also must be compatible with desiccants. Ageless Type Z, is especially suitable for use with dry materials, and can be used with desiccants. The capacity of the oxygen absorber to remove oxygen in a sealed container is another factor which should be considered. One bag of Ageless-Z 300 has the capacity to absorb 300 $cm^3$ of oxygen, which corresponds to an air volume of 1500 $cm^3$. The removal of oxygen is critical to prevent oxidative damage to the organism during long term storage.

Alternatively, the oxygen can be substantially removed from the package at the time of sealing by the application of vacuum, or by flushing the package with nitrogen before sealing.

Materials Used to Deplete or Remove Moisture

A variety of desiccants can be used to remove moisture from the packaging. For example, Drierite™, anhydrous calcium sulfate, is commercially available from W. A. Hammond Drierite Company, P.O. Box 460, Xenia, Ohio 45385. Drierite™ is a suitable desiccant that can be used in microbial pesticide packaging systems because it will not release any of its absorbed water when exposed to high ambient temperatures. The water is securely held in the form of the hemi-hydrate of calcium sulfate which requires temperatures in excess of 350° F. (177° C.) to free the water. This is an important characteristic for shipping microbial products during variable weather conditions. For the drying of gases, Drierite™ has a water capacity of 10 to 14 weight percent. One Drierite desiccant bag will reduce the humidity in a sealed enclosure to a −100° F. (−73° C.) dew point in about 10 hours or less. One bag containing 28 grams of calcium sulfate is used with a container of 24 cm×14 cm, having a volume of about 200 to 250 $cm^3$. Other compounds such as silica, certain clays, polyacrylic acid derivatives, and other desiccants may also be used to reduce the water content of the bacteria.

Methods for Packaging

The dried microorganisms are sealed within the pouch material using conventional methods known to those skilled in the art, such as heat sealing. The dried microorganisms are sealed within the smallest pouch that will contain them, with no excess air or water being included at the time of the sealing, to the extent possible.

In a preferred embodiment, the organisms are produced by submerged fermentation and harvested with a carrier, resulting in a biomass. The biomass is then dried to remove the free and most bound water from the biomass, and placed in pouches made of a material such as aluminum foil or foil laminates which are impermeable to gas and water vapor transmission. The biomass is then sealed in each pouch with desiccant and oxygen scavenger. Pouches may be stored at room temperature and opened when the biomass is ready for use.

The bacterial formulations packaged in this system typically can survive for a long period of time at 20° C., and for at least ten months at 30° C. with minimal viability loss.

The formulated biomass can subsequently be rehydrated and applied as a biocontrol agent using drench, dip, spray, or other delivery systems to control pre-harvest, post-harvest, and soil borne diseases. It may also be combined with solid carriers to facilitate delivery of the active substance. Examples include those described above, although other compositions may be added to facilitate application. Formulations can be in the form of a dust, granule, wettable granule, wettable powder or a tablet. In a preferred embodiment, the aggregate moisture content of the formulation is such that the organism is in a dormant state generally at a percent water content is less than 10%.

The present invention will be further understood by reference to the following non-limiting examples.

EXAMPLE 1

Preparation of Dry Bacterial Formulation

A preferred composition is a fibrous growth medium such as rockwool in which an appropriate biocontrol agent is inoculated. The agent is selected, grown, suspended, and concentrated approximately 100 fold from the nutrient medium. A rockwool growth medium is prepared by sterilizing, preferably by autoclaving, to remove potential contaminants and then drying to remove all moisture, preferably by air drying using a fluid bed dryer. The suspended agent was administered into the rockwool in a quantity of 1 ml of suspended agent into a plug of 2.5 cm length by 2 cm diameter. This size plug appears to be optimum for drying. Greater quantities of agent may be applied, however, if preferable.

A 1 ml freezer stock of *Pseudomonas cepacia* was added to Tryptic soy broth plus glucose (TSBG) and grown at 20° C. The resultant suspension was concentrated 100-fold.

Rockwool plugs were autoclaved to remove contaminants. They were then dried overnight in an oven to remove all moisture so that an accurate dry weight of the plugs could be obtained.

A 1 ml aliquot of the concentrated *P. cepacia* was pipetted into each rockwool plug. One group of plugs was allowed to equilibrate for one hour. The second group of plugs was allowed to equilibrate for twenty four hours. The rockwool plugs were then dried in a Lab Line Instruments Fluidized Bed Dryer at a temperature of 50° C. Drying took approximately 60 to 80 minutes. The plugs were weighed periodically throughout the drying period to assess whether they had reached their original dry weight.

Once the plugs with the *P. cepacia* had been dried to their original weight, they were packaged in foil laminate pouches. Two plugs were sealed in each pouch with approximately 28 g of Drierite® desiccant and 28 g of Ageless® oxygen remover. The two groups of plugs were then sampled periodically over a 35 day time frame to determine whether the *P. cepacia* remained viable. Bacteria are counted as colony forming units or CFUs. Bacterial populations showed no significant drop in viable population. The results are shown in Table 1.

TABLE 1

| Viability of Bacterial Formulations | | |
|---|---|---|
| | Viable Population (log cfus/plug) | |
| Time (days) | group 1 | group 2 |
| 1 | 7.30 | — |
| 7 | 7.18 | 7.68 |
| 14 | 7.26 | 7.85 |
| 35 | 6.48 | 7.53 |

EXAMPLE 2

Determination of the Effect of Moisture and Oxygen on Bacteria

Rockwool plugs were prepared as in example 1 and packaged. The packaging and internal environment was varied to determine the effect of oxygen and environmental moisture content on the stability of the dried bacteria. Both foil packaging and polyethylene packaging were used with and without desiccant and oxygen scavenger. The foil packaging is impermeable to oxygen and water vapor and the polyethylene packaging is permeable to both.

The bacteria were evaluated for viability after one week and again after two weeks. The results are shown in Table 2. This data clearly demonstrates that the bacteria was stable only when kept in a low oxygen, low moisture content environment. After a period of only two weeks, the samples exposed to oxygen and moisture showed a clear decline in bacterial population. The samples exposed to the greatest concentrations of oxygen and moisture, those packaged in the permeable polyethylene without desiccant or oxygen scavenger, experienced the most immediate and significant drop in bacterial population.

TABLE 2

| Effect of Moisture and Oxygen on Bacterial Viability. | | | |
|---|---|---|---|
| | Bacterial enumerations (log cfus/plug) | | |
| Packaging | week 0 | week 1 | week 2 |
| Foil with Desiccant and Oxygen Scavenger | 7.59 | 7.11 | 7.91 |
| Foil without Desiccant and Oxygen Scavenger | 7.59 | 6.61 | 3.99 |
| Polyethylene with Desiccant and Oxygen Scavenger | 7.59 | 6.11 | 4.29 |
| Polyethylene, without Desiccant and Oxygen Scavenger | 7.59 | <3.00 | <3.00 |

EXAMPLE 3

Prevention of Pythium Infection in Cucumbers Using Stabilized *P. cepacia* in Rockwool This experiment was conducted to demonstrate the effect of fluid bed drying on the efficacy of a bacterial biocontrol agent.

*P. cepacia* was grown in TSBG (Difco tryptic soy broth+ 1.75% glucose). The culture was centrifuged, the supernatant discarded, and the pellet resuspended in a 0.085 NaCl solution. A total viable count (TVC) was taken using 0.085% NaCl solution dilution tubes and TSBA (Difco tryptic soy broth+1.5% agar) as the plating medium. The plates were incubated at room temperature for two days, at which time the number of colony forming units (CFUs)/plate was determined to be $1.05 \times 10^{10}$ CFUs/ml.

Rockwool plugs of approximately 2.5 cm in diameter and 2.0 cm in length were placed in a pipette tip container and autoclaved. After autoclaving, the plugs were divided into two groups. Group 1 was inoculated with 1 ml of TSBG and group 2 was inoculated with 2 ml of TSBG. A 10 µl portion of a 1/10 dilution of the *P. cepacia* culture was added to each plug. The inoculated plugs were incubated in a biocontainment hood overnight.

After 24 hours of incubation, the number of CFU's/plug had increased to $1.12 \times 10^{10}$/ml for group 1 and $3.11 \times 10^{10}$/ml for group 2. The plugs were then dried to a constant weight using a Lab Line Instruments Fluid Bed Dryer set at 50° C. The plugs from group 1 were dried for 20 minutes and the plugs from group 2 for 50 minutes. After drying the CFU's in both groups dropped to $1.67 \times 10^8$ and $1.3 \times 10^8$, respectively.

Five groups of twelve plugs were placed in a rockwool well. This is an inert material with an indentation of a diameter slightly larger than that of the rockwool plug. The five groups included the two dried groups, along with an untreated rockwool plug, a plug treated with fresh *P. cepacia* and a rockwool plug treated with Pythium. Each plug was placed in a separate well. A cucumber seed was also added to each well. The resulting concentration of the *P. cepacia* in the well was approximately $10^7$ CFU/well for the *P.cepacia*/TSBG treatments. The fresh *Pseudomonas cepacia* concentration was approximately $5.1 \times 10^7$/well.

Results are shown in table 3.

TABLE 3

Comparison of the biocontrol activity of *P. cepacia* inoculated plugs to a fresh *P. cepacia* culture.

| Treatment | Number of seeds infected |
|---|---|
| Untreated Control | 0 |
| Pathogen Control | 10 |
| Fresh *P. cepacia* | 0 |
| Dried *P. cepacia* (group #1) | 0 |
| Dried *P. cepacia* (group #2) | 0 |

EXAMPLE 4

Formulation of *P. syringae*

*Pseudomonas syringae* deposited with the ATCC as strain designation number 55389 was obtained. The bacteria was harvested by centrifugation and mixed with attapulgite clay such that the bacteria constituted 10% of the formulation by weight. The formulation was then dried in a fluid bed dryer for 40 minutes at 110° C. until the formulation approached a percent water content of approximately 4%. The bacterial mixture was then identically packaged in foil laminate pouches, which are extremely water and gas impermeable. Each pouch contained Drierite® desiccant and Ageless® oxygen remover. These pouches maintain a substantially oxygen free and low humidity environment.

Figure 7:
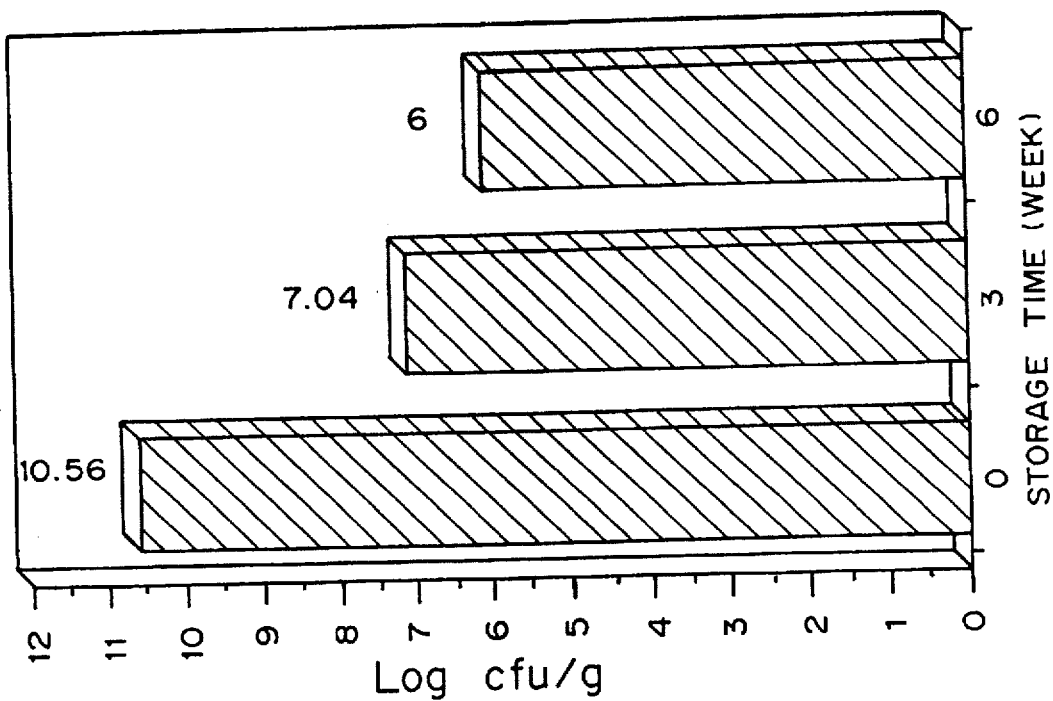
Figure 5:
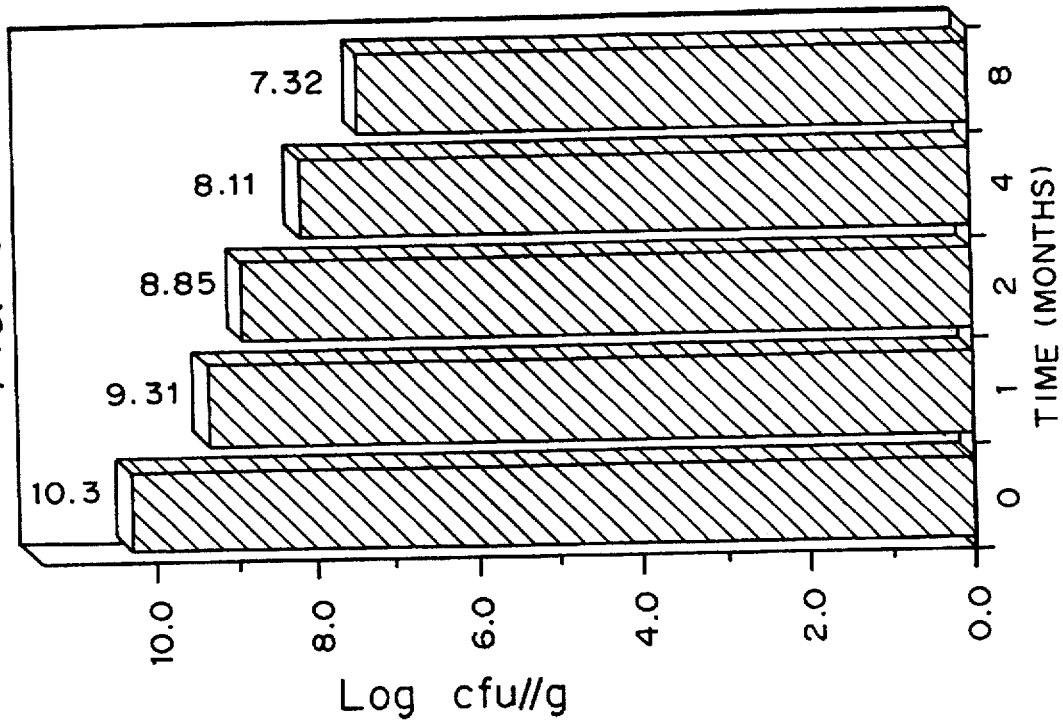

The pouches were stored at 5° C., 20° C., 25° C., 30° C. and 37° C., respectively. The stability of the packaged formulations is shown in FIGS. 1, 2, 3, 4, and 5 over a period of eight or ten months. The bacterial mixture was also placed in test tubes with screw caps and stored at 20° C. for six weeks. Stability was analyzed at three week intervals. The results shown in FIG. 7 demonstrate that unpackaged bacteria is unstable even at room temperature.

The resulting data is significant as it demonstrates that the packaging system provides for a stable shelf life for a bacterial biocontrol agent at room temperature, generally 20° to 25° C. The data also demonstrates that even at extreme temperatures, 30° to 37° C., there is only a minimal loss in viability, which is essential for a commercial product. It is also vital that the product not lose significant viability during transport when the temperature may reach extremes.

Figure 6:
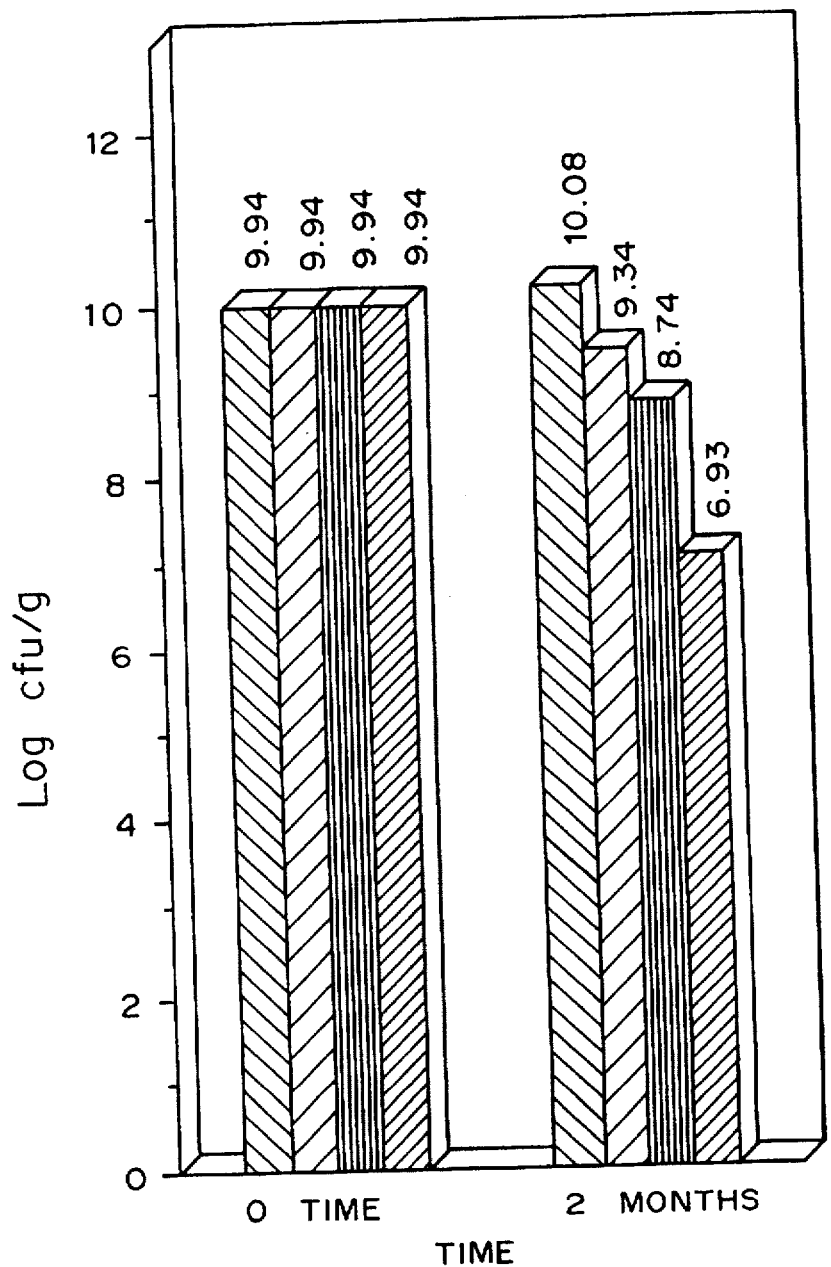

FIG. 6 is a graph of the stability of the 10% wettable powder formulation stored at 25° C. with a desiccant and oxygen remover versus that stored at 25° C. which has been vacuum packaged. The data shows the variability between two packaging systems, but indicates that both are equally effective. It particularly highlights the importance of achieving very low levels of oxygen content for maximal stability. Some oxygen is still left with vacuum packaging and the organisms do not store as well.

EXAMPLE 5

Efficacy of Stored Bacterial Formulation

*Pseudomonas syringae* was prepared and packaged as in example 4 and stored for one year. Efficacy of the bacterial formulation was determined at the conclusion of storage at 5° C., 20° C. and 30° C. for one year. Packages were opened and 0.5 grams of the *Pseudomonas syringae* formulation were removed from each. This was added to 5 mls of water and the solution was then diluted ten fold. 10 µls of each dilution were plated ten times to microbiological media and incubated for 48 hours at 28° C. The samples were then held in the refrigerator for two days. CFU's per ml was determined by counting the number of colonies.

Granny Smith apples were then treated. Ten microliters of $1 \times 10^4$ cfu's/ml of *Penicillium expansium* as the pathogen and of *Pseudomonas syringae* as biocontrol agent were applied to each apple at three wound sites per apple. One control sample (#1) was treated with only deionized water and one control (#2) was treated with only the pathogen.

The apples were evaluated based on lesions at each wound site. The absence of lesions at the wound site demonstrated control of the pathogen. The results are shown in Table 2. This example demonstrates that the formulated bacterium not only remain viable after long term storage, but also remain efficacious.

TABLE 4

| Efficacy of *Pseudomonas syringae* stored for twelve months at 5° C., 20° C. and 30° C. | | | | |
|---|---|---|---|---|
| sample | storage temperature | *P. syringae* (CFU/wound) | Number lesions/ number wounds | lesion size (mm) |
| control #1 | N.A. | 0.0 | 0/00 | 0.0 |
| control #2 | N.A. | 0.0 | 9/9 | 22.2 |
| 1 | 5° C. | $3.0 \times 10^6$ | 0/3 | 0.0 |
| 2 | 5° C. | $3.0 \times 10^6$ | 0/3 | 0.0 |
| 3 | 5° C. | $3.0 \times 10^6$ | 0/3 | 0.0 |
| 4 | 20° C. | $3.0 \times 10^6$ | 0/3 | 0.0 |
| 5 | 20° C. | $2.7 \times 10^6$ | 0/3 | 0.0 |
| 6 | 20° C. | $2.8 \times 10^6$ | 0/3 | 0.0 |
| 7 | 30° C. | $6.2 \times 10^5$ | 0/3 | 0.0 |
| 8 | 30° C. | $5.0 \times 10^5$ | 0/3 | 0.0 |
| 9 | 30° C. | $1.1 \times 10^4$ | 0/3 | 0.0 |

EXAMPLE 6

Stability of *P. syringae* Under Commercial Storage Conditions

*Pseudomonas syringae* NRRL B-18739 was formulated and packaged as described in example 4. Three samples were then stored for one month in a residential garage to simulate typical storage conditions for a commercial product. This allowed for the unregulated rise and fall in temperatures that would occur in a commercial situation during shipment and storage of the product.

Viability studies were conducted prior to the packaging and at the conclusion of the experiment. The results are shown in Table 5. This study demonstrates that bacteria will remain viable even under unregulated field conditions.

TABLE 5

| | Viability of Bacterial under Commercial Storage Conditions. | |
|---|---|---|
| Sample | Initial Viability (log cfu/g) | Viability at One Month (log cfu/g) |
| 1 | 10.91 | 10.69 |
| 2 | 10.72 | 10.66 |
| 3 | 10.79 | 10.71 |

Modifications and variations of the method for producing stabilized bacteria and bacterial formulations will be obvious to those skilled in the art from the foregoing detailed description. Such modifications and variations are intended to come within the scope of the following claims.

We claim:

1. A method for preparing a stabilized bacterial formulation which retains viability when stored at a temperature between about 20° to 25° C. for at least a year, the method comprising drying harvested bacteria at temperatures which do not kill the bacteria, until free and bound water has been removed, wherein the bacteria become dormant, which is 10% by weight of the bacteria or less, wherein the bacteria is mixed with a powder or granular inert non-aqueous carrier, and packaging the dried bacteria and carrier in a sealed packaging material which is impermeable to gas and water vapor transfer, and removing substantially all of the oxygen from the package.

2. The method of claim 1 wherein the bacteria are selected from the group consisting of Pseudomonas species, Enterobacter species, and Bacillus species.

3. The method of claim 1 wherein the moisture content is less than 4% by weight.

4. The method of claim 1 wherein the oxygen content is zero.

5. The method of claim 1 wherein the oxygen is removed by addition of an oxygen absorbing or scavenging agent to the packaging.

6. The method of claim 1 wherein the water content is reduced by addition of a dessicant to the packaging.

7. The method of claim 1 wherein the carrier is selected from the group consisting of attapulgite clays, kaolinite clays, montmorillonites, saponites, mica, perlites, vermiculite, talcs, carbonates, rockwool, sulfates, diatomites, and synthetic silicates.

8. The method of claim 1 further comprising including with the carrier a surfactant.

9. The method of claim 1 further comprising including with the carrier a dispersant.

10. The method of claim 1 wherein the bacteria and the carrier are dried using a fluid bed dryer.

11. A stabilized bacterial formulation retaining viability when stored at a temperature between about 20° to 25° C. for at least a year comprising bacteria which have been harvested and then dried at temperatures which do not kill the bacteria, until free and bound water has been removed, wherein the bacteria become dormant, which is 10% by weight or less, and a non-aqueous powder or granular inert carrier, contained within a sealed packaging material, which is impermeable to gas and water vapor transfer and contains substantially no oxygen.

12. The formulation of claim 11 wherein the bacteria are selected from the group consisting of Pseudomonas species, Enterobacter species, and Bacillus species.

13. The formulation of claim 11 wherein the moisture content is less than 4% by weight.

14. The formulation of claim 11 further comprising an oxygen absorbing or scavenging agent.

15. The formulation of claim 11 further comprising a desiccant.

16. The formulation of claim 11 wherein the bacteria is in combination with a dry carrier, dessicant and oxygen scavenger.

17. The formulation of claim 16 wherein the carrier is selected from the group consisting of attapulgite clays, kaolinite clays, montmorillonites, saponites, mica, perlites, vermiculite, talcs, carbonates, sulfates, diatomites, synthetic silicates, and rockwool.

18. The formulation of claim 16 further comprising a surfactant.

19. The formulation of claim 16 further comprising a dispersant.

* * * * *